(12) United States Patent
Nachum et al.

(10) Patent No.: US 11,752,336 B2
(45) Date of Patent: *Sep. 12, 2023

(54) ELECTRICAL DEVICE FOR PROVIDING PAIN RELIEF

(71) Applicant: IPULSE MEDICAL LTD., Tiberius (IL)

(72) Inventors: Zvi Nachum, Tiberius (IL); Shalom Lampert, Maalot (IL)

(73) Assignee: IPULSE MEDICAL LTD., Tiberius (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/720,168

(22) Filed: Apr. 13, 2022

(65) Prior Publication Data

US 2022/0233858 A1  Jul. 28, 2022

Related U.S. Application Data

(63) Continuation of application No. 16/323,177, filed as application No. PCT/IB2017/054965 on Aug. 15, 2017, now Pat. No. 11,331,481.

(30) Foreign Application Priority Data

Aug. 15, 2016 (GB) ..................... 1613950

(51) Int. Cl.
  *A61N 1/36* (2006.01)
  *A61N 1/04* (2006.01)
(52) U.S. Cl.
  CPC ....... *A61N 1/36021* (2013.01); *A61N 1/0484* (2013.01); *A61N 1/36007* (2013.01); *A61N 1/36034* (2017.08)
(58) Field of Classification Search
  None
  See application file for complete search history.

(56) References Cited

U.S. PATENT DOCUMENTS

| 4,232,680 A | 11/1980 | Hudleson et al. |
| 4,237,899 A | 12/1980 | Hagfors et al. |

(Continued)

FOREIGN PATENT DOCUMENTS

| CN | 1956749 A | 5/2007 |
| EP | 0057048 A1 | 8/1982 |

(Continued)

OTHER PUBLICATIONS

Machine Translation for CN1956749 (Google Patents) published on May 2, 2007.

(Continued)

*Primary Examiner* — Catherine M Voorhees
*Assistant Examiner* — Elizabeth K So
(74) *Attorney, Agent, or Firm* — Momentum IP; Marc Van Dyke

(57) ABSTRACT

An apparatus for relieving pain in a region of the body of a user by contacting electrodes to a surface of the body of the user at the region and providing a series of electrical impulses to the region, the apparatus including: (a) at least two electrodes adapted to contact a surface of a body of the user; (b) a control unit; and (c) a signal generator, associated with the control unit and responsive thereto, the signal generator and the control unit adapted to operative connect to a power supply, the signal generator adapted, in an operative mode, to provide a series of electrical impulses to the surface of the body, via the electrodes, the series including a plurality of cycles, each of the cycles having a positive voltage pulse and a negative voltage pulse, wherein a frequency of the plurality of cycles is optionally within a range of 60-150 cycles per second, wherein a time-averaged voltage amplitude ($Va_p$) of the positive voltage pulse, over an entire duration ($Tp_{positive}$) thereof, is 20-90 Volts, and wherein a ramp-up section of the positive voltage pulse (Continued)

fulfills at least one of the following structural conditions: (1) the positive voltage pulse attains at least 80% of the time-averaged voltage amplitude, within a time (T80) of 70-150 nanoseconds; (2) the positive voltage pulse increases by at least 20 Volts, within 70 nanoseconds.

20 Claims, 8 Drawing Sheets

(56) References Cited

U.S. PATENT DOCUMENTS

| | | | |
|---|---|---|---|
| 4,580,570 | A | 4/1986 | Sarrell et al. |
| 6,136,019 | A | 10/2000 | Mower |
| 11,331,481 | B2 * | 5/2022 | Nachum ............ A61N 1/36007 |
| 2003/0158585 | A1 | 8/2003 | Burnett |
| 2007/0270917 | A1 | 11/2007 | Nachum |
| 2007/0299482 | A1 | 12/2007 | Littlewood et al. |
| 2009/0112283 | A1 | 4/2009 | Kriksunov et al. |
| 2010/0274327 | A1 | 10/2010 | Carroll |
| 2011/0178571 | A1 | 7/2011 | Tannebaum et al. |
| 2012/0109233 | A1 | 5/2012 | Lee |
| 2014/0249601 | A1 | 9/2014 | Bachinski |
| 2016/0022987 | A1 | 1/2016 | Zschaeck et al. |
| 2016/0051817 | A1 | 2/2016 | Popovic et al. |

FOREIGN PATENT DOCUMENTS

| | | |
|---|---|---|
| EP | 2774651 A1 | 9/2014 |
| JP | 2010184113 A | 8/2010 |
| JP | 2013094330 A | 5/2013 |
| JP | 2014121631 A | 7/2014 |
| JP | 2016512707 A | 5/2016 |
| WO | 9936124 A1 | 7/1999 |
| WO | 2015/145813 A1 | 10/2015 |

OTHER PUBLICATIONS

International Search Report for PCT/IB2017/054965 dated Dec. 20, 2017.
Written Opinion for PCT/IB2017/054965 dated Dec. 20, 2017.
Machine Translation for JP2010184113 (Google Patents) published on Aug. 26, 2010.
Machine Translation for JP2013094330 (Google Patents) published on May 20, 2013.
Machine Translation for JP2014121631 (Google Patents) published on Jul. 3, 2014.
Machine Translation for JP2016512707 (Google Patents) published on May 9, 2016.
Machine Translation for WO2015/145813 (Google Patents) published on Oct. 1, 2015.

* cited by examiner

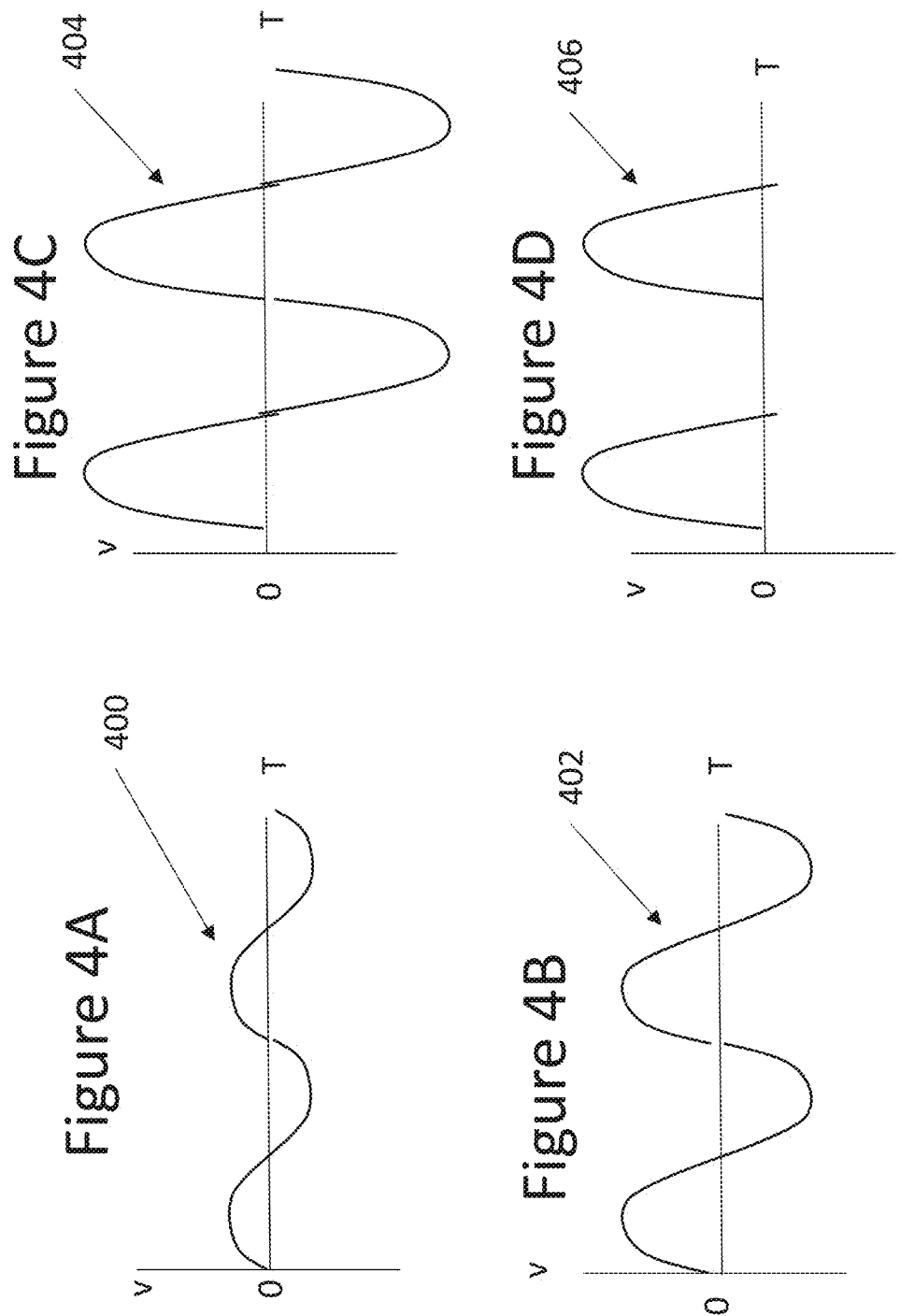

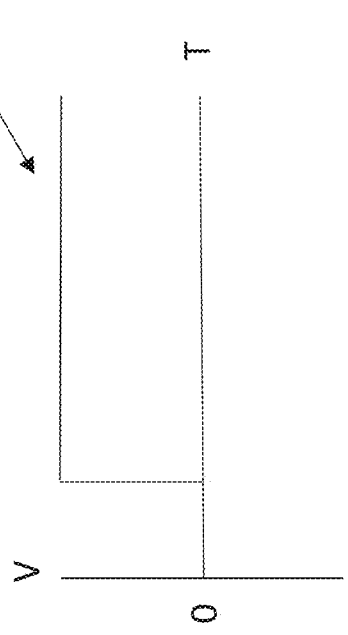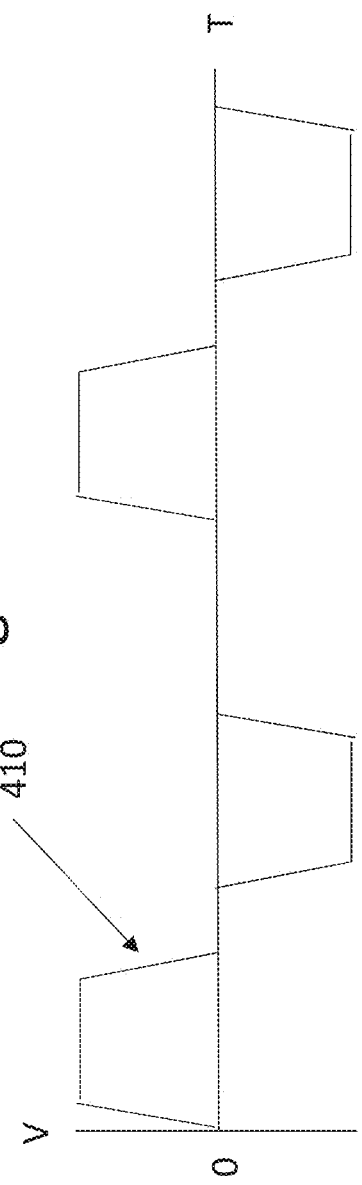

ELECTRICAL DEVICE FOR PROVIDING PAIN RELIEF

RELATED APPLICATIONS

PCT/IB2017/054965 filed on Aug. 15, 2017 is incorporated herein by reference as if fully set forth herein.

FIELD OF THE INVENTION

The present invention relates to devices and methods for providing pain relief, and particularly to electrical devices and methods providing pain relief by providing electrical impulses to a surface of the body at a region at which pain is experienced.

SUMMARY OF THE INVENTION

According to some teachings of the present invention there is provided a non-invasive device for providing pain relief to a human user, the device including: (a) at least two electrodes adapted to contact a surface of a body of the user; (b) a control unit; and (c) a signal generator, associated with the control unit and responsive thereto, the signal generator and the control unit adapted to operative connect to a power supply, the signal generator adapted, in an operative mode, to provide a series of electrical impulses to the surface of the body, via the electrodes, the series including a plurality of cycles, each of the cycles having a positive voltage pulse and a negative voltage pulse, wherein a frequency of the plurality of cycles is optionally within a range of 60-150 cycles per second, wherein a time-averaged voltage amplitude ($Va_p$) of the positive voltage pulse, over an entire duration ($Tp_{positive}$) thereof, is 20-90 Volts, and wherein a ramp-up section of the positive voltage pulse fulfills at least one of the following structural conditions: (1) the positive voltage pulse attains at least 80% of the time-averaged voltage amplitude, within a time (T80) of 70-150 nanoseconds; (2) the positive voltage pulse increases by at least 20 Volts, within 70 nanoseconds.

According to further teachings of the present invention there is provided a non-invasive device for providing pain relief to a human user, the device including: (a) at least two electrodes adapted to contact a surface of a body of the user; (b) a control unit; and (c) a signal generator, associated with the control unit and responsive thereto, the signal generator and the control unit adapted to operative connect to a power supply, the signal generator adapted, in an operative mode, to provide a series of electrical impulses to the surface of the body, via the electrodes, the series including a plurality of cycles, each of the cycles having a positive voltage pulse and a negative voltage pulse, wherein a time-averaged voltage amplitude ($Va_p$) of the positive voltage pulse, over an entire duration ($Tp_{positive}$) thereof, is 20-90 Volts, wherein a ramp-up section of a the positive voltage pulse of cycles in a first subset of the plurality of cycles has a first ramp up time, a ramp-up section of a the positive voltage pulse of cycles in a second subset of the plurality of cycles, following the first subset, has a second ramp up time, shorter than the first ramp up time, and wherein the ramp-up section of the positive voltage pulse of the cycles in the second subset fulfills at least one of the following structural conditions: (1) the positive voltage pulse attains at least 80% of the time-averaged voltage amplitude, within a time (T80) of 70-150 nanoseconds; (2) the positive voltage pulse increases by at least 20 Volts, within 70 nanoseconds.

According to further teachings of the present invention there is provided a method for providing pain relief to a user, the method including: (a) providing a device as described herein; (b) attaching the at least two electrodes to the surface of the body of the user; and (c) activating the signal generator to operate in the operative mode to provide the series of electrical impulses to the surface of the body, via the electrodes.

According to further features in the described preferred embodiments, the attaching includes attaching the at least two electrodes to the surface of the body at a region at which pain is felt by the user.

According to still further features in the described preferred embodiments, the region at which pain is felt by the user is an abdominal area of the user.

According to still further features in the described preferred embodiments, the method is effected so as to provide relief to menstrual or pre-menstrual pains.

According to still further features in the described preferred embodiments, the method further includes the user wearing the device.

According to still further features in the described preferred embodiments, the wearing includes attaching the device to a garment worn by the user.

According to still further features in the described preferred embodiments, the wearing includes wearing the device while the device is in the operative mode.

According to still further features in the described preferred embodiments, the device is portable, the method further including the user moving a distance of at least ten, at least five, or at least three meters while wearing the device, in the operative mode, for at least 10, at least 5, or at least 3 minute.

According to still further features in the described preferred embodiments, T80 is at least 75 nanoseconds.

According to still further features in the described preferred embodiments, T80 is at least 80 nanoseconds.

According to still further features in the described preferred embodiments, T80 is at most 140 nanoseconds.

According to still further features in the described preferred embodiments, T80 is at most 130 nanoseconds.

According to still further features in the described preferred embodiments, T80 is at most 120 nanoseconds.

According to still further features in the described preferred embodiments, T80 is at most 115 nanoseconds.

According to still further features in the described preferred embodiments, T80 is at most 110 nanoseconds.

According to still further features in the described preferred embodiments, the positive voltage pulse increases by at least 20 Volts, within 70 nanoseconds.

According to still further features in the described preferred embodiments, the positive voltage pulse increases by at least 30 Volts, within 70 nanoseconds.

According to still further features in the described preferred embodiments, the positive voltage pulse increases by at least 40 Volts, within 70 nanoseconds.

According to still further features in the described preferred embodiments, the positive voltage pulse increases by at least 50 Volts, within 70 nanoseconds.

According to still further features in the described preferred embodiments, an intermediate time (Ti) between the positive voltage pulse and the negative voltage pulse is at least 0.1 milliseconds, at least 0.2 milliseconds, at least 0.3 milliseconds, or at least 0.4 milliseconds.

According to still further features in the described preferred embodiments, the intermediate time (Ti) is at most 1 millisecond, at most 0.9 milliseconds, at most 0.8 milliseconds, or at most 0.7 milliseconds.

According to still further features in the described preferred embodiments, the positive pulse attains at least 80% of the time-averaged voltage amplitude for a pulse duration within a range of 70-130 microseconds, 80-120 microseconds, or 90-110 microseconds.

According to still further features in the described preferred embodiments, the positive pulse has a substantially constant voltage amplitude for a pulse duration within a range of 70-130 microseconds, 80-120 microseconds, or 90-110 microseconds.

According to still further features in the described preferred embodiments, the frequency of the plurality of cycles is within a range of 70-140 cycles per second, 80-130 cycles per second, or 80-120 cycles per second.

According to still further features in the described preferred embodiments, the negative voltage pulse is area-symmetric with respect to the positive voltage pulse, within 10 area %, within 5 area %, within 2 area %, or within 1 area %.

According to still further features in the described preferred embodiments, the positive voltage pulse attains at least 80%, at least 85%, at least 90%, at least 95%, or substantially 100% of the time-averaged voltage amplitude, within 70-150 nanoseconds.

According to still further features in the described preferred embodiments, the signal generator includes a low voltage signal generator adapted to produce a low voltage AC signal, the low voltage signal generator producing a peak voltage of up to 10.0 volts up to 5.0 volts.

According to still further features in the described preferred embodiments, the signal generator includes at least one of a voltage pre-amplifier and a voltage amplifier, adapted to amplify the voltage of a signal provided as input thereto.

According to still further features in the described preferred embodiments, the voltage pre-amplifier and/or the voltage amplifier is disposed electrically downstream with respect to a low voltage signal generator, and receives as input a the low voltage AC signal generated by the low voltage signal generator.

According to still further features in the described preferred embodiments, the signal generator includes a transformer adapted to amplify the voltage of a signal provided as input thereto.

According to still further features in the described preferred embodiments, the transformer is disposed electrically downstream with respect to the voltage pre-amplifier and the voltage amplifier.

According to still further features in the described preferred embodiments, the signal generator includes an AC-to-DC converter disposed electrically downstream relative to the transformer and adapted to produce a substantially DC signal from an input signal provided thereto.

According to still further features in the described preferred embodiments, the signal generator includes an AC-to-DC converter adapted to produce a substantially DC signal.

According to still further features in the described preferred embodiments, the AC-to-DC converter is disposed electrically downstream with respect to the voltage pre-amplifier and the voltage amplifier.

According to still further features in the described preferred embodiments, the AC-to-DC converter includes a diode circuit adapted to produce the substantially DC signal.

According to still further features in the described preferred embodiments, the diode circuit includes at least one diode, and a capacitor disposed electrically downstream of the at least one diode.

According to still further features in the described preferred embodiments, the signal generator includes a switching mechanism, responsive to the control unit, adapted to transform an input signal provided to the switching mechanism into the series of electrical impulses.

According to still further features in the described preferred embodiments, the switching mechanism receives as the input signal a substantially DC signal.

According to still further features in the described preferred embodiments, the switching mechanism includes a first switch, responsive to the control unit, adapted to generate from the substantially DC signal the positive voltage pulses of the series, and a second switch, responsive to the control unit, adapted to generate from the substantially DC signal the negative voltage pulses of the series.

According to still further features in the described preferred embodiments, the power supply includes a low voltage power supply adapted to provide a nominal voltage of at most 10 volts, at most 8.0 volts, at most 6.0 volts, at most 5.0 volts, at most 4.0 volts, or at most 3.0 volts.

According to still further features in the described preferred embodiments, the device further includes a housing enclosing the control unit, the signal generator, and the power supply.

According to still further features in the described preferred embodiments, in the operative mode, the power supply enclosed in the housing is the sole power supply for the device.

According to still further features in the described preferred embodiments, the housing has dimensions within the range of 4 cm×4 cm×8 mm to 6 cm×6 cm×13 mm.

According to still further features in the described preferred embodiments, the device has a weight in the range of 90 to 150 grams, excluding any power supply enclosed in the housing.

According to still further features in the described preferred embodiments, the device is portable while in the operative mode.

According to still further features in the described preferred embodiments, the electrodes are adapted to contact the surface of the body of the user at a region of the body at which pain is experienced.

According to still further features in the described preferred embodiments, a ramp-up section of a positive voltage pulse of cycles in a third subset of the plurality of cycles, following the second subset, has a third ramp up time, which is shorter than the second ramp up time.

According to still further features in the described preferred embodiments, a time-averaged voltage amplitude ($Va_n$) of the negative voltage pulse, over an entire duration ($Tp_{negative}$) thereof, is 20-90 Volts.

According to still further features in the described preferred embodiments, a ramp-up section of the negative voltage pulse fulfills at least one of the following structural conditions: (1) the negative voltage pulse attains at least 80% of the time-averaged voltage amplitude, within a time (T80) of 70-150 nanoseconds; (2) the negative voltage pulse decreases by at least 20 Volts, within 70 nanoseconds.

According to still further features in the described preferred embodiments, the ramp-up section of the negative voltage pulse decreases by at least 20 Volts, at least 30 Volts, at least 30 Volts, or at least 50 Volts, within 70 nanoseconds.

According to still further features in the described preferred embodiments, the negative pulse attains at least 80% of the time-averaged voltage amplitude for a pulse duration within a range of 70-130 microseconds, 80-120 microseconds, or 90-110 microseconds.

According to still further features in the described preferred embodiments, the negative pulse has a substantially constant voltage amplitude for a pulse duration within a range of 70-130 microseconds, 80-120 microseconds, or 90-110 microseconds.

According to still further features in the described preferred embodiments, the negative voltage pulse attains at least 80%, at least 85%, at least 90%, at least 95%, or substantially 100% of the time-averaged voltage amplitude, within 70-150 nanoseconds.

BRIEF DESCRIPTION OF THE FIGURES

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like functionalities, but not necessarily identical elements.

In the drawings:

FIGS. 4A-4F are schematic illustrations of pulses transmitted from different components of the signal generator of FIG. 2 in accordance with an embodiment of the teachings herein;

DETAILED DESCRIPTION

Systems and methods are described herein that apply electrical impulses to the surface of the body of a user at a region of the body at which pain is experienced, thereby to relieve the pain.

Figure 1:
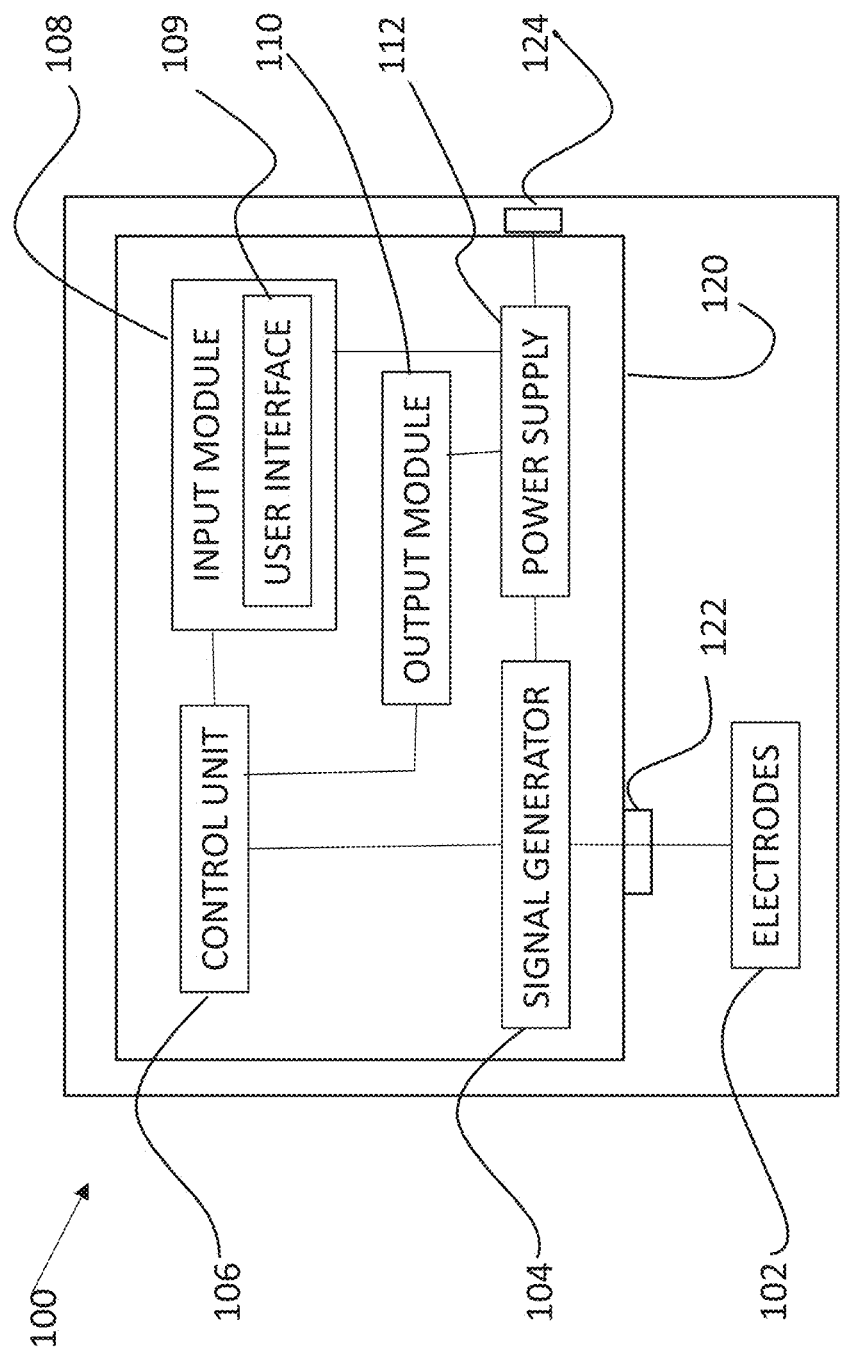
FIG. 1 is a schematic block diagram of an embodiment of an inventive device for providing pain relief utilizing an inventive series of electrical impulses, according to an embodiment of the teachings herein.

Reference is now made to FIG. 1, which is a schematic block diagram of an embodiment of an inventive device for providing pain relief utilizing an inventive series of electrical impulses according to an embodiment of the teachings herein.

As seen, a device 100 for providing pain relief may include at least two stimulating electrodes 102, which are functionally associated with a signal generator 104. The electrodes 102 receive from signal generator 104 an electrical signal to be provided to the surface of the skin of the user. The stimulating electrodes 102 are adapted to contact a surface of the body of the user at a region of the body at which pain is experienced, and, in an operative mode, to deliver electrical impulses to the surface of the body as described hereinbelow.

The signal generator 104 is functionally associated with, and receives instructions from, a control unit 106, which may, in some embodiments, be functionally associated with an input module 108 for providing input to the control unit 106, and with an output module 110 via which control unit 106 provides an output to the user. The control unit may be any suitable control unit, such as an 8/16 bit AVR® XMEGA® microcontroller commercially available from Atmel® of San Jose, Calif., USA.

In some embodiments, the input module 108 includes, or may be associated with, a user interface 109 including an on/off switch for activating and/or terminating activation of the device 100.

In some embodiments, user interface 109 includes one or more adjustment buttons or settings for increasing and decreasing the desired peak voltage.

In some embodiments, the signal generator 104, control unit 106, input module 108, and output module 110 may be electrically associated with and powered by one or more power supplies 112. In some embodiments, the power supply 112 is a low voltage power supply, providing a nominal voltage of at most 10.0 volts, at most 8.0 volts, at most 6.0 volts, at most 5.0 volts, at most 4.0 volts, or at most 3.0 volts. In some embodiments, the power supply includes at least one rechargeable battery, such as at least one nickel-metal hydride (NiMH) battery, nickel-cadmium (NiCd) battery, lithium-ion (Li-ion) battery, or lithium polymer (Li-Poly) battery. In some embodiments, the device 100 is powered solely by power provided by the rechargeable battery, and does not require connection to an additional power supply for functioning thereof when the rechargeable battery is sufficiently charged.

The signal generator 104, control unit 106, and power supply 112 may be enclosed in a housing 120, which may include a port 122 for connection of the electrodes 102 to the signal generator 104, and/or a port 124 for connection of the power supply 112 to an external power source, for example for connection of a charging cable connected to an electrical socket.

In some embodiments, the device has dimensions within the range of 4 cm×4 cm×8 mm to 6 cm×6 cm×13 mm, and more typically, within the range of 4 cm×4 cm×9 mm to 5.3 cm×5.3 cm×12 mm. The weight of the device, excluding the battery, is 90 to 150 grams, and more typically, 100 to 125 grams.

In some embodiments, the device 100 may be readily be worn by the user, for example clipped onto a garment thereof. In some embodiments, the device 100 is portable, and can function in its operative signal providing mode while being transported, or moved, from one place to another, or while the user is in motion.

Figure 2:
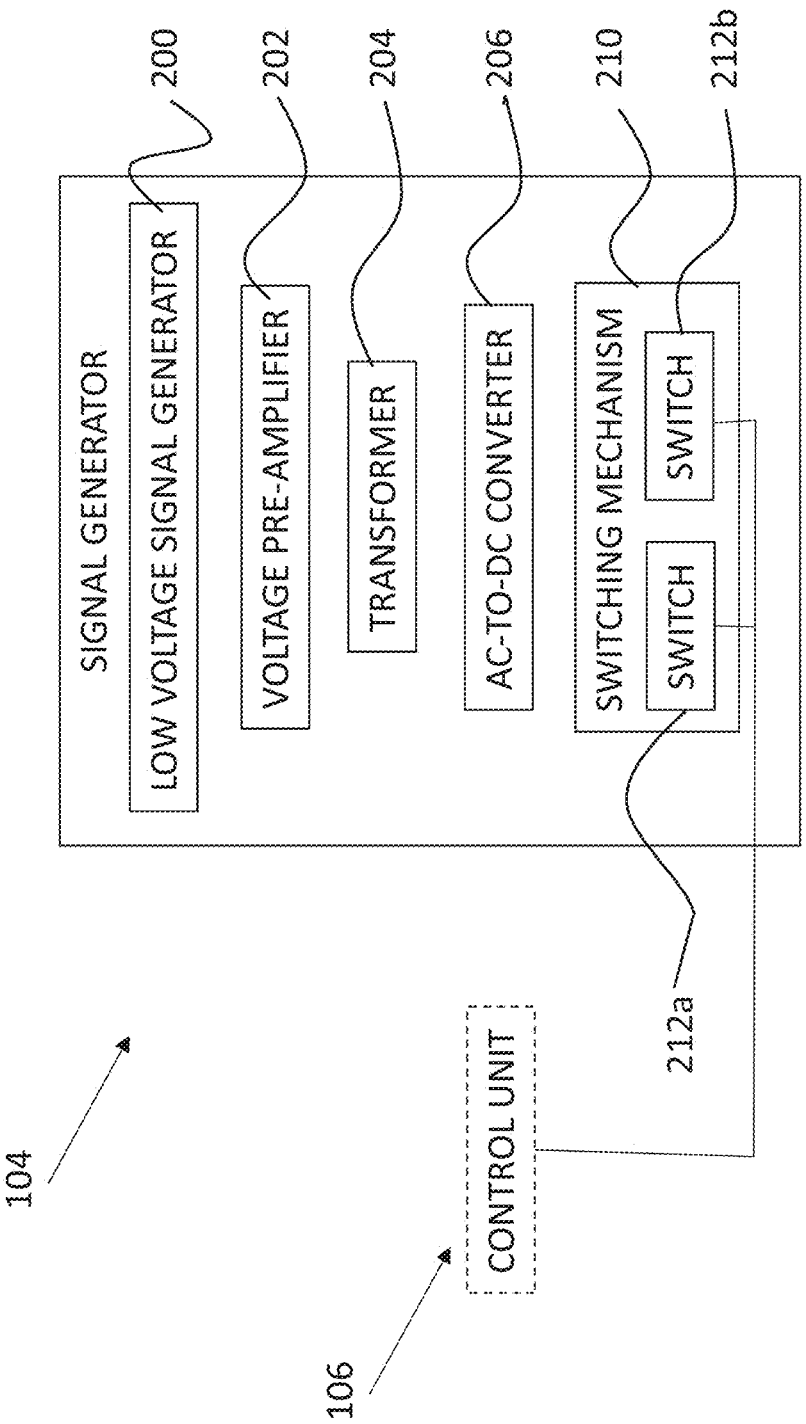
FIG. 2 is a schematic block diagram of a signal generator according to an embodiment of the teachings herein, the signal generator forming part of the device of FIG. 1.

Reference is now additionally made to FIG. 2, which is a schematic block diagram of signal generator 104 of device 100 according to an embodiment of the teachings herein.

Signal generator 104 may optionally include a signal generator such as a low voltage signal generator 200, which generates an alternating current (AC) signal 400 as shown in FIG. 4A. In some embodiments, the signal generated by low voltage signal generator 200 has a peak voltage within the range of 3.0-10.0 volts, and more typically, within the range of 3.0-5.0 volts.

In some embodiments, the signal 400 generated by low voltage signal generator 200 may be provided to a voltage pre-amplifier 202. The voltage pre-amplifier 202 increases the voltage of the received signal, to generate a new AC signal 402 having a higher voltage, as shown in FIG. 4B. In some embodiments, the voltage pre-amplifier 202 may be replaced by a voltage amplifier having similar functionality.

In some embodiments, power supply 112 (shown in FIG. 1) can deliver a voltage directly to any one of components 200, 202, 204, or 206.

In some embodiments, power supply 112 can deliver a high DC voltage (e.g., at least 20 volts) directly to switching mechanism 210.

The signal 402 output by pre-amplifier 202 is provided to a transformer 204, such as an LPR6235 transformer commercially available from Coilcraft® Inc. of Cary, Ill., USA. At the expense of reduced current output, transformer 204 increases the voltage of the received signal, to generate a new AC signal 404 having a higher voltage than signal 402, as seen in FIG. 4C.

The signal 404 output by transformer 204 is provided to an AC-to-DC converter 206. In some embodiments, such as the embodiment illustrated in FIG. 3, the AC-to-DC converter 206 includes a diode circuit 300 including at least one diode 302 and a capacitor 304 disposed downstream thereto. Signal 404 output by the transformer 204 is provided as input to the diode 302, which selects from the signal 404 the positive voltage segments, resulting in the signal 406 illustrated in FIG. 4D. It is appreciated that the negative voltage segments may be obtained from signal 404 by reversing the direction of diode 302, as is known in the art.

The signal 406 generated by the diode 302, and in some embodiments also the corresponding signal generated by the reversed diode 302, is provided as input to the capacitor 304, which converts the signal into a DC signal 408 having a fixed voltage, as illustrated in FIG. 4E.

The DC signal 408 output by capacitor 304 is provided as input to a switching mechanism 210, such as a BSS123LT1G or a BVSS123LT1G commercially available from ON Semiconductor® of Phoenix, Ariz., USA.

In some embodiments, the switching mechanism includes a first switch 212a generating a positive pulse of the generated signal, and a second switch 212b generating a negative pulse of the generated signal, as described in further detail hereinbelow. Switching mechanism 210, and in some embodiments, each of switches 212a and 212b, may be controlled by control unit 106 to produce signal 410, illustrated in FIG. 4F. Signal 410 is provided to the electrodes 102 and therefrom to the surface of the user's body. Signal 410 and characteristics thereof are described in further detail hereinbelow with respect to FIG. 5B.

Figure 5A:
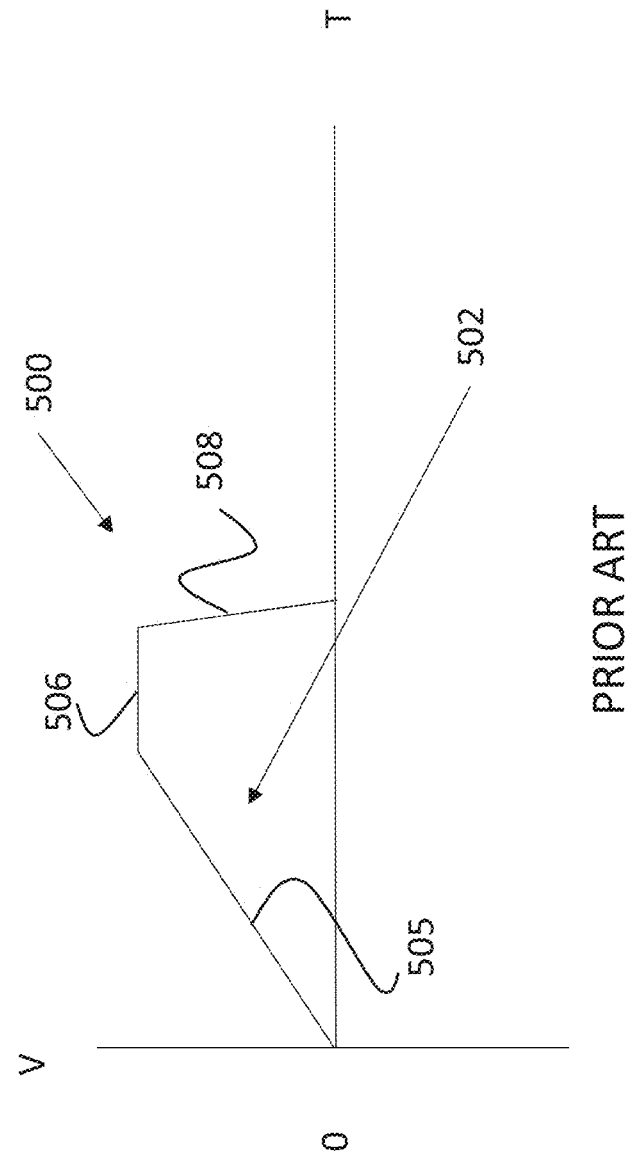
FIG. 5A is a schematic illustration of an electrical signal transmitted by prior art devices for relief of pain.
Figure 5B:
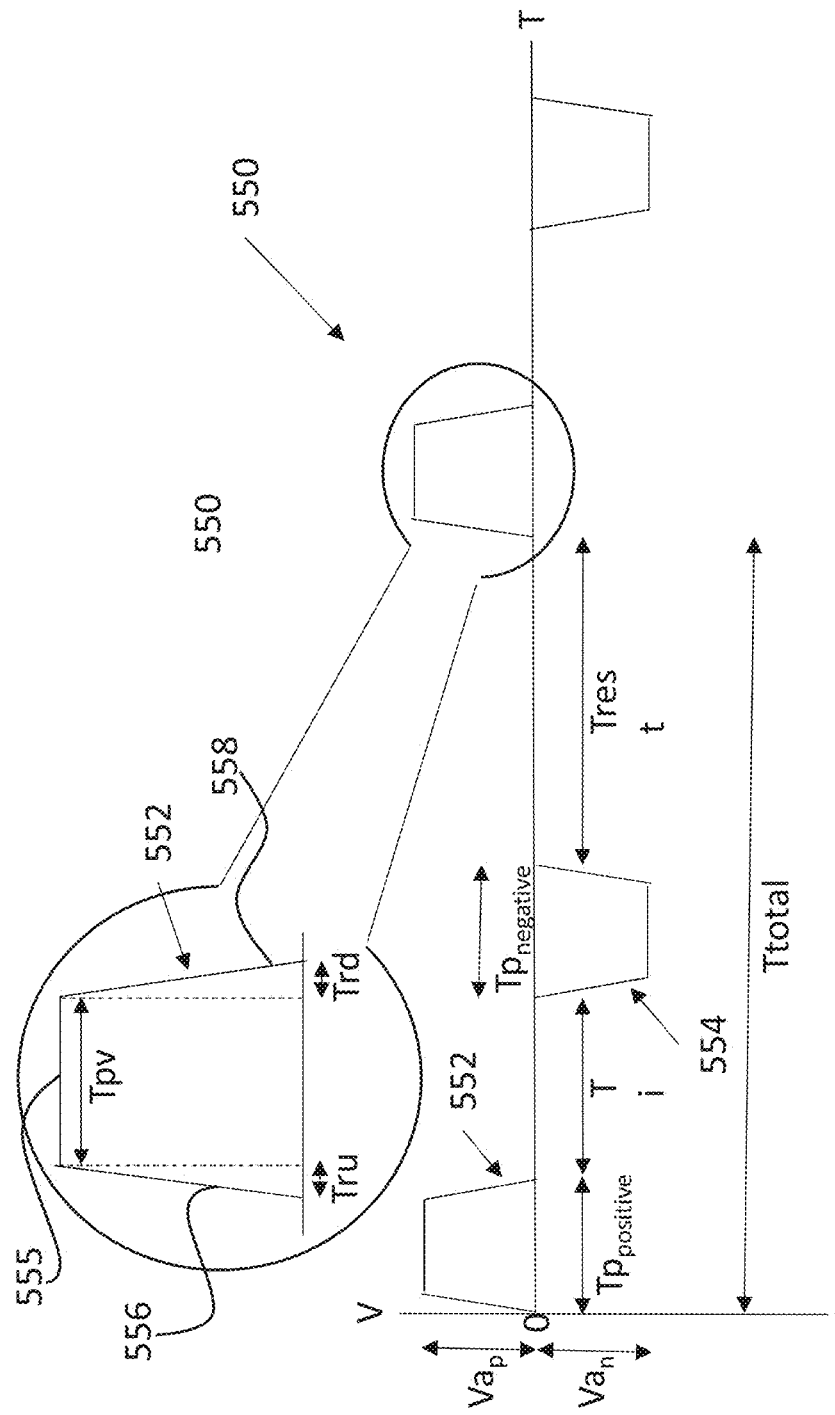
FIG. 5B is a schematic illustration of an inventive electrical signal according to the teachings herein, which may be generated by the signal generator of FIG. 2.

Reference is additionally made to FIG. 5A, which is a schematic illustration of an electrical signal transmitted by prior art devices for relief of pain, and to FIG. 5B, which is a schematic illustration of an inventive electrical signal according to the teachings herein, which may be generator by the signal generator of FIG. 2. It will be appreciated that the signals in FIGS. 5A and 5B are not drawn to scale, and are not intended to limit the durations of different portions of the signals, only to provide an understanding of the structures and shapes of these signals.

As seen in FIGS. 5A, prior art devices for relief of pain provide a signal 500 defining a pulse 502. Pulse 502 has a total pulse time (Tp), which includes: (a) a ramp-up time (Tru), indicated by segment 505 of the pulse, (b) a peak-voltage time (Tpv), indicated by segment 506 of the pulse, and (c) a ramp down time (Trd), indicated by segment 508 of the pulse.

The peak voltage is defined as a voltage within 15%, within 10%, within 5%, within 3%, or within 1% of the maximal voltage in the pulse. The maximal voltage in the pulse is the highest voltage attained by a positive voltage pulse, or the lowest voltage attained by a negative voltage pulse, during the entire duration of the pulse.

The ramp-up time (Tru) is generally the time in which the voltage of the pulse increases, or transitions, to at least 80%, at least 85%, at least 90%, at least 95%, or substantially 100% of the peak voltage or of the maximal voltage of the signal. Typically, the ramp up time includes an increase in voltage from a baseline voltage, which is typically zero. Conversely, the ramp-down time (Trd) is generally the time in which the voltage of the pulse decreases, or transitions, from the peak voltage of maximal voltage for the signal by at least 80%, at least 85%, at least 90%, at least 95%, or at substantially 100% of the voltage, or to a voltage that is at most 20%, at most 15%, at most 10%, at most 5%, or substantially equal to the baseline voltage, typically zero.

The ramp-up time Tru of prior art devices may be at least 0.5 microseconds, and more typically, in the range of 0.5-1 microseconds (500-1000 nanoseconds).

Figure 3:
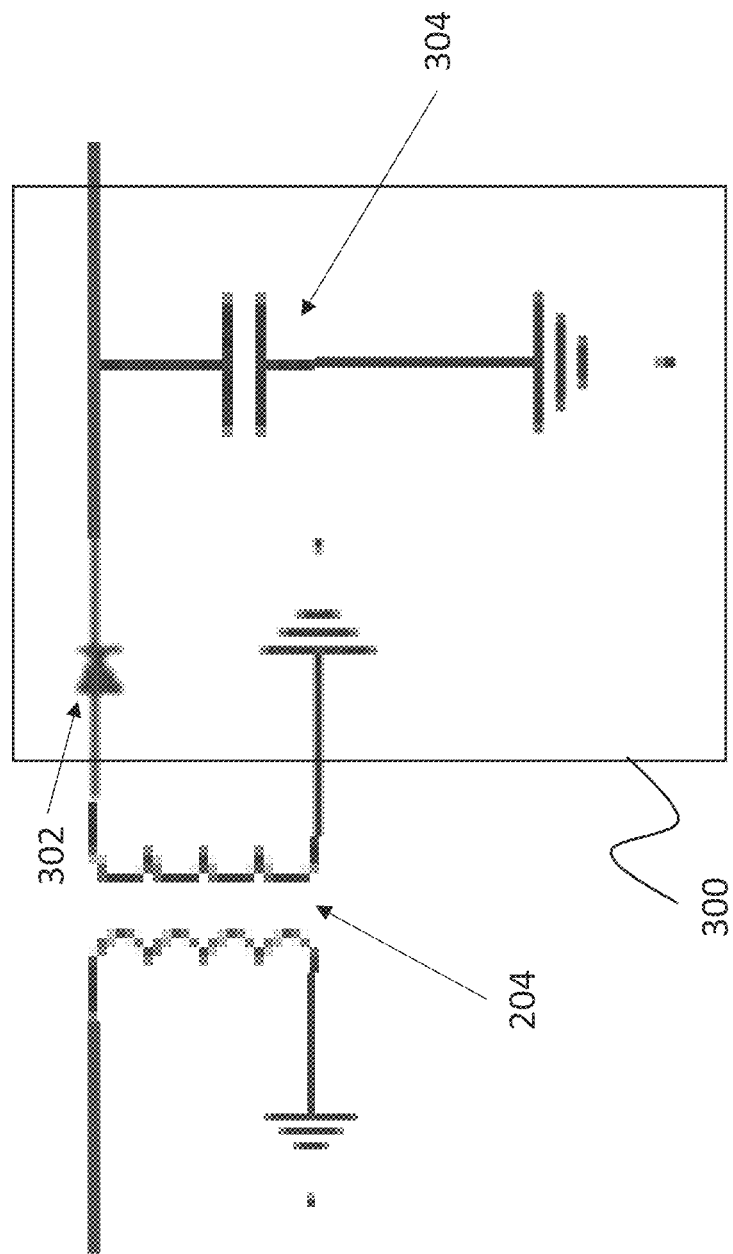
FIG. 3 is a simplified electrical chart of a transformer and an AC-to-DC signal converter according to the teachings herein, the transformer and AC-to-DC signal converter forming part of the signal generator of FIG. 2.

Turning to FIG. 5B, it is seen that a signal 550 provided by the inventive device 100 of FIGS. 1-3 includes multiple cycles, each cycle being bi-phasic and including a positive voltage pulse 552 having a positive voltage and a negative voltage pulse 554 having a negative voltage. Each of positive voltage pulse 552 and negative voltage pulse 554 has a total pulse time (Tp) (indicated as $Tp_{positive}$ for the positive voltage pulse 552 and as $Tp_{negative}$ for the negative voltage pulse 554), which includes a ramp-up time (Tru), a peak-voltage time (Tpv), and a ramp down time (Trd). For each of the positive and negative voltage pulses 552 and 554, a ramp up segment of the pulse is indicated by reference numeral 556, a ramp down segment of the pulse is indicated by reference numeral 558, and a peak voltage segment of the pulse is indicated by reference numeral 555. It will be appreciated that the ramp-up segment 556 of the positive voltage signal 552 is achieved by the control unit 106 operating switch 212a. The ramp down segment 558 may be provided passively, by the switch 212a or switching mechanism 210 stopping operation to provide a signal, or may alternately be provided actively, by the switch 212a actively lowering the voltage provided by pulse 552.

Similarly, it will be appreciated that the ramp-up segment 556 of the negative voltage signal 554 is provided by the control unit 106 operating switch 212b. The ramp down segment 558 may be provided passively, by the switch 212b or switching mechanism 210 stopping operation to provide a signal, or may alternately be provided be provided actively, by the switch 212b actively increasing the voltage provided by pulse 554.

In some embodiments, the positive voltage pulse 552 has a time-averaged voltage amplitude ($Va_p$), over the entire duration ($Tp_{positive}$) thereof, in the range of 20-90 Volts, and the negative voltage pulse 554 has a time-averaged voltage amplitude ($Va_n$), over the entire duration ($Tp_{negative}$) thereof, in the range of −20--90 Volts.

The ramp up time (Tru) and ramp down time (Trd) are defined as discussed hereinabove with respect to FIG. 5A. It will be appreciated by people of skill in the art that in the positive voltage pulse 552, the peak voltage is a positive voltage, and as such during the ramp up time the voltage increases from the baseline voltage, typically zero, towards the peak voltage, and during the ramp down time the voltage decreases from the peak voltage towards the baseline voltage, whereas in the negative voltage pulse 554 the peak voltage is a negative voltage, and as such during the ramp up time the voltage decreases from the baseline voltage towards the peak voltage, and during the ramp down time the voltage increases from the peak voltage back towards the baseline voltage.

Specifically, it is a particular feature of the teachings herein that the positive voltage pulse 552 attains at least 80% of the time-averaged voltage amplitude ($Va_p$) within a time (T80) of 70-150 nanoseconds, and/or that the positive voltage pulse 552 increases by at least 20 Volts within 70 nanoseconds. Similarly, the negative voltage pulse 554 attains at least 80% of the negative time-averaged voltage amplitude ($Va_n$) within a time (T80) of 70-150 nanoseconds, and/or decreases by at least 20 Volts within 70 nanoseconds.

In some embodiments, T(80) is at least 75 nanoseconds or at least 80 nanoseconds. In some embodiments, T(80) is at most 140 nanoseconds, at most 130 nanoseconds, at most 120 nanoseconds, at most 115 nanoseconds, or at most 110 nanoseconds.

In some embodiments, the positive voltage pulse 552 increases by at least 30 Volts, by at least 40 Volts, or by at least 50 Volts, within 70 nanoseconds. In some embodiments, the negative voltage pulse 554 decreases by at least 30 Volts, by at least 40 Volts, or by at least 50 Volts, within 70 nanoseconds.

In some embodiments, the positive voltage pulse 552 attains at least 80%, at least 85%, at least 90%, at least 95%, or substantially 100% of the time-averaged voltage amplitude ($Va_p$) within 70-150 nanoseconds, 75-140 nanoseconds, 80-130 nanoseconds, 80-120 nanoseconds, or 80-110 nanoseconds.

In some embodiments, the negative voltage pulse 554 attains at least 80%, at least 85%, at least 90%, at least 95%, or substantially 100% of the time-averaged voltage amplitude ($Va_n$) within 70-150 nanoseconds, 75-140 nanoseconds, 80-130 nanoseconds, 80-120 nanoseconds, or 80-110 nanoseconds.

As such, in some embodiments, the ramp-up time (Tru), which is controlled by switching mechanism 210, is in the range of 50-200 nanoseconds, 60-175 nanoseconds, 70-150 nanoseconds, 75-140 nanoseconds, 80-130 nanoseconds, 80-120 nanoseconds, or 80-110 nanoseconds.

As is clearly understood from comparison of FIGS. 5A and 5B, the ramp-up time (Tru) during which the prior art pulse 502 ramps up to reach the peak voltage, is significantly longer than the ramp-up time during which the positive voltage pulse 552 of the present invention reaches the peak voltage. The inventor has surprisingly discovered that the short ramp-up time is associated with improved alleviation of pain and discomfort, including alleviation of physiological pain and/or of instrumentally induced pain, if such exists.

More specifically, the inventor has found that at a ramp-up time of less than 70 ns, the instrumentally-induced pain greatly increases, and is not sufficiently compensated for by the pain-relief mechanisms of the body. The inventor has further found that at ramp-up times in excess of 200 ns, the instrumentally induced pain may be greatly reduced, but activation of the pain-relief mechanisms of the body (e.g., generation of opiates or morphine-like substances) is also greatly reduced, such that such slow ramp-up times are relatively inefficacious in alleviating the pain of the user.

Without wishing to be bound by theory, Applicants believe that the rapid ramp up of the signal provided by the present invention at the region of the body at which pain is felt by the user, causes the brain to send to that region a significantly increased amount of opiates or morphine-like molecules, which provide rapid and effective pain relief to the area, and which also provide immediate and substantially complete relief to any pain experienced by the user due to provision of the signal, such that the signal does not, in and of itself, cause the user pain, and the enhanced presence of opiates or morphine-like molecules in that area of the body relieve the previously felt pain for which the user is receiving treatment.

Stated differently, Applicants believe that the provision of the electrical signals to the area at which the pain is felt, occupies the pain feeling neurons in the area, resulting in the brain providing pain relieving molecules to the area in a quantity which is sufficient for effectively eliminating the pain felt by the provision of the signal, if any, and for relieving the pain for which treatment is being sought. An intermediate time (Ti), is defined as the time between the positive voltage pulse 552 and the negative voltage pulse 554, and a rest time (Trest), is defined as the rest time between cycles, or as the time from the end of the negative voltage pulse 554 of one cycle and the beginning of the positive voltage pulse 552 of the next cycle. The total time for each cycle (Ttotal) is defined as Ttotal=$Tp_{positive}$+$Tp_{negative}$+Ti+Trest.

In some embodiments, the frequency of the cycles in signal 550 is in the range of 60-150 cycles per second, 70-140 cycles per second, 80-130 cycles per second, or 80-120 cycles per second. Stated differently, the total time (Ttotal) for each cycle is in the range of 6.5-16.7 milliseconds, in the range of 7.1-14.3 milliseconds, in the range of 7.7-12.5 milliseconds, or in the range of 8.3-12.5 milliseconds.

In some embodiments, the total pulse time (Tp) for each of the positive and negative voltage pulses 552 and 554 is in the range of 70-130 microseconds, in the range of 80-120 microseconds, or in the range of 90-110 microseconds. In some embodiments, the positive pulse attains at least 80% of $Va_p$, and/or the negative pulse attains at least 80% of $Va_n$, for a pulse duration within the range of 70-130 microseconds, in the range of 80-120 microseconds, or in the range of 90-110 microseconds. In some embodiments, the positive voltage pulse and/or the negative voltage pulse has a substantially constant voltage amplitude for a pulse duration within a range of 70-130 microseconds, 80-120 microseconds, or 90-110 microseconds.

In some embodiments, the intermediate time (Ti) for each cycle is at least 0.1 millisecond, at least 0.2 milliseconds, at least 0.3 milliseconds, or at least 0.4 milliseconds. In some embodiments, the intermediate time (Ti) for each cycle is at most 1 millisecond, at most 0.9 milliseconds, at most 0.8 milliseconds, or at most 0.7 milliseconds.

In some embodiments, the rest time (Trest) between the end of a final voltage impulse of a particular cycle, and the beginning of an initial voltage impulse of a subsequent, adjacent particular cycle is at least 0.3 milliseconds, at least 0.4 milliseconds, or at least 0.5 milliseconds. In some embodiments, Trest for each cycle is at most 1 millisecond, at most 0.9 milliseconds, at most 0.8 milliseconds, or at most 0.7 milliseconds.

In some embodiments, the negative voltage pulse 554 is area-symmetric with respect to the positive voltage pulse 552, within 10 area %, within 5 area %, within 2 area %, or within 1 area %. Stated differently, the cumulative charge provided by the negative voltage pulse 554 to the surface of the body of the user is within 10%, 5%, 2%, or 1% of the cumulative charge provided by the positive voltage pulse 552 to the surface of the body of the user. As such, in some embodiments, each cycle in the signal 550 is a balanced bi-phasic cycle.

Figure 6:
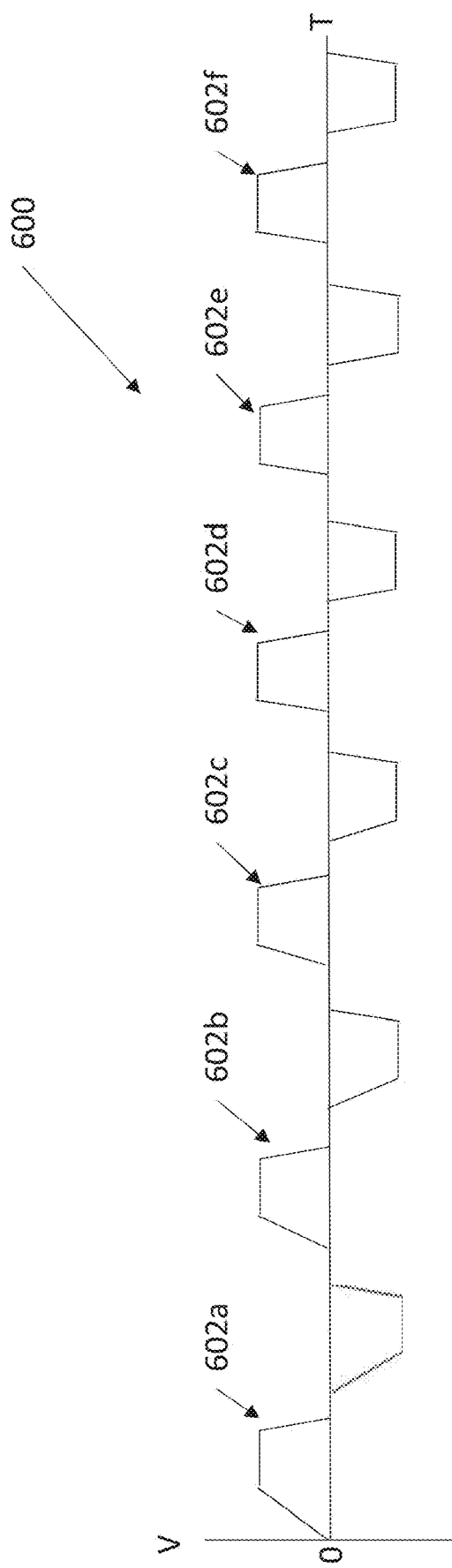
FIG. 6 is a schematic illustration of a series of electrical signals according to an embodiment of the teachings herein.

Reference is now made to FIG. 6, which is a schematic illustration of a series of electrical signals according to an embodiment of the teachings herein. As shown, an electrical signal 600 includes a plurality of cycles 602, each including a positive voltage pulse 604 having a similar structure to that of positive voltage pulse 552 of FIG. 5B and a negative voltage pulse 606 having a similar structure to that of negative voltage pulse 554 of FIG. 5B.

In each cycle 602, the ramp-up time (Tru) of the positive voltage pulse is substantially equal to the ramp up time of the negative voltage pulse, but the ramp up times are different between cycles. More specifically, with each cycle 602 the ramp up time Tru decreases or gradually decreases, until the ramp-up time of 70-150 nanoseconds, described in detail with respect to FIG. 5B, is reached.

As such, in the first cycle 602a, or in a first sequence of such cycles, the positive and negative voltage pulses have a relatively long ramp up time, which may, in some embodiments, be greater than 100 nanoseconds, or in the range of 100-200 nanoseconds. In subsequent cycles, or sequences of cycles, the positive and negative voltage pulses have increasingly shorter ramp-up times. For example, the second cycle 602b, or second sequence of cycles, may have a ramp-up time of 100 nanoseconds, the third cycle 602c, or third sequence of cycles, may have a ramp up time of 95 or 90 nanoseconds, and so on, until the ramp up time reaches the desired ramp-up time, for example 80 nanoseconds, shown in the two last illustrated cycles, 602e and 602f. It will be appreciated that in accordance with the teachings herein, any additional cycles following cycle 602f will continue to have a ramp-up time in the range of 70-150 nanoseconds, as described hereinabove.

Without wishing to be bound by theory, the inventor believe that the signal shown in FIG. 6 would eliminate any residual pain caused by provision of the signal, in that such pain would not be generated due to the relatively long ramp-up time of the first cycle 602a, and that that the pulses provided in cycle 602a would cause the body to deliver to the region at which the electrodes are placed sufficient pain relieving molecules, such as opiates or morphine-like molecules, to relieve any pain felt by the somewhat shorter ramp up time of the pulses in signal 602b. The inventor believes that this behavior would continue and sufficient pain relieving molecules would be present at the beginning of each cycle, other than cycle 602a, such that no pain would be felt by the user due to the provision of the signal—in cycle 602a because the ramp up time is sufficiently long so as not to cause pain as is known in the art, and in the following cycles because sufficient pain relieving molecules will have been delivered to the vicinity of the electrodes and would alleviate any pain potentially caused by the provision of the signals.

A device such as the devices described in conjunction with any of FIGS. 1-3 may be provided to a user. In typical use, the user or clinician attaches the electrodes 102 to a surface of the body, in a general area where pain is experienced. In some embodiments, the pain is a menstrual or pre-menstrual pain, and the user attaches the electrodes to the skin surface at or near an abdominal region of the body, where the pain is experienced.

Once the electrodes are attached to the skin of the user, the user uses the user interface 109 to activate the device 100, such processor 106 activates signal generator 104 to provide signals as described in FIG. 5B to the skin surface of the user's body, thereby to relieve the pain. In some embodiments, the user may then provide input to processor 106 via input module 108 and/or user interface 109 thereof, for example to indicate whether the treatment is helping, to increase or decrease the frequency or intensity of the signals, or to terminate activity of device 100.

In some embodiments, the user may wear the device, before, after, and during operation thereof, for example clipped to a garment worn by the user. In such embodiments, the device 100 is portable, and as such may be used in the operative mode, while worn by the user and/or solely using the on-board power supply, when the user is moving around, without being tied to a specific location, for a duration of at least 5 minutes, at least 10 minutes, at least 15 minutes, or at least 30 minutes.

As used herein in the specification and in the claims section that follows, the term "or" is considered as inclusive, and therefore the phrase "A or B" means any of the groups "A", "B", and "A and B".

As used herein in the specification and in the claims section that follows, the terms "pulse", "signal", and "impulse" all relate to an electrical signal, for example applied via an electrode.

As used herein in the specification and in the claims section that follows, the term "cycle" relates to a repetitive or semi-repetitive bi-phasic segment of an electrical voltage signal, as is generally recognized and understood in the art. Represented on a voltage vs. time plot, a "cycle" typically consists of a positive voltage pulse, a negative voltage pulse, any intermediate time (Ti) therebetween, and the rest time (Trest) between the end of a final voltage impulse of a particular cycle, and the beginning of an initial voltage impulse of a subsequent, adjacent particular cycle. As a matter of convention, Trest≥Ti.

As used herein in the specification and in the claims section that follows, the term "positive voltage pulse" relates to an electrical pulse providing an electrical signal having positive voltage, whether an absolute positive voltage or a positive voltage relative to a baseline voltage. Typically the baseline voltage is zero.

As used herein in the specification and in the claims section that follows, the term "negative voltage pulse" relates to an electrical pulse providing an electrical signal having negative voltage, whether an absolute negative voltage or a negative voltage relative to a baseline voltage. Typically the baseline voltage is zero.

As used herein in the specification and in the claims section that follows, the term "peak voltage" relates to a voltage within 15%, within 10%, within 5%, within 3%, or within 1% of the maximal voltage in the pulse. The peak voltage of a positive voltage pulse is a positive voltage and the peak voltage of a negative voltage pulse is a negative voltage.

As used herein in the specification and in the claims section that follows, the term "peak voltage time" relates to the duration in which the pulse attains the peak voltage.

As used herein in the specification and in the claims section that follows, the term "maximal voltage" relates to the highest voltage attained by a positive voltage pulse, or the lowest voltage attained by a negative voltage pulse, during the entire duration of the pulse. As used herein in the specification and in the claims section that follows, the term "ramp-up time" relates to the time in which the voltage of the pulse, or the absolute value or magnitude of the voltage of the pulse, increases to at least 80%, at least 85%, at least 90%, at least 95%, or substantially 100%, of the peak voltage.

As used herein in the specification and in the claims section that follows, the term "ramp-down time" relates to the time in which the voltage of the pulse, or the absolute value or magnitude of the voltage of the pulse, decreases by at least 80%, at least 85%, at least 90%, at least 95%, or substantially 100%, of the peak voltage, or to be within 20%, within 15%, within 10%, within 5%, or substantially equal to, the baseline voltage.

As used herein in the specification and in the claims section that follows, the term "timed-averaged voltage amplitude" relates to the average voltage amplitude over a predetermined time duration, for example the average voltage amplitude for a positive or negative voltage pulse over the entire duration thereof, or over a segment of the positive or negative voltage pulse at which a peak voltage amplitude is attained. Due to the extremely swift ramp-up times utilized in the present invention, the "timed-averaged voltage amplitude" of the "plateau" of such a pulse may be approximated by the "timed-averaged voltage amplitude" of the pulse, or the "timed-averaged voltage amplitude" of the portion of the pulse in which voltage is applied, e.g., taken over the ramp-up time (Tru) and the peak-voltage time (Tpv).

As used herein in the specification and in the claims section that follows, the term "substantially constant voltage amplitude", with regard to a voltage pulse, or a portion thereof, relates to a voltage amplitude being constant, within a deviation of 15%, 10%, 5%, 3%, or 1%.

As used herein in the specification and in the claims section that follows, the term "area-symmetric" relates to two voltage pulses, such as a positive voltage pulse and a negative voltage pulse, which, when an amplitude thereof is plotted relative to time and relative to a baseline voltage or relative to a zero voltage, the areas trapped between the plots of the two pulses' amplitudes and of the baseline voltage are equal, or are within 10%, within 5%, within 2%, within 1%, of one another.

As used herein in the specification and in the claims section that follows, the term "balanced cycle" relates to a cycle including a positive voltage pulse and a negative voltage pulse, such that the charge provided by the positive and negative voltage signals is equal, or is within 15%, within 10%, within 5%, within 3%, or within 1% of one another.

As used herein in the specification and in the claims section that follows, the term "A is electrically downstream to B" relates to an electrical component A which receives, as input, an electrical signal provided by an electrical component B, either directly or via additional electrical components located electrically between electrical components B and A.

As used herein in the specification and in the claims section that follows, the term "portable" relates to a device which can be ported, or moved around, while in its operative mode using an on-board power supply, to a distance greater than 10 meters and/or for a duration of at least 5 minutes, at least 10 minutes, at least 15 minutes, or at least 30 minutes, without requiring a wired or wireless connection to a power source or to a communication module such as a Wi-Fi transceiver.

As used herein in the specification and in the claims section that follows, the term "instrumentally induced pain" relates to any pain or discomfort caused by operation of the device or instrument on or in the body of the user to provide treatment thereto.

As used herein in the specification and in the claims section that follows, the terms "physiological pain" and "physiologically induced pain" relate to pain caused by the physiology of the user, irrespective of the presence or operation of a device or instrument on or in the body of the user.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. Similarly, the content of a claim depending from one or more particular claims may generally depend from the other, unspecified claims, or be combined with the content thereof, absent any specific, manifest incompatibility therebetween.

As used herein, unless otherwise stated, the terms "substantially" and "about", when modifying a condition or relationship characteristic of a feature or features of an embodiment of the present technology, are to be understood to mean that the condition or characteristic is defined to within tolerances that are acceptable for operation of the embodiment for an application for which it is intended.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A non-invasive device for providing pain relief to a human user, the device comprising:
   (a) at least two electrodes adapted to contact a surface of a body of the user;
   (b) a control unit; and
   (c) a signal generator, associated with said control unit and responsive thereto, said signal generator and said control unit adapted to operative connect to a power supply,
   said signal generator adapted, in an operative mode, to provide a series of electrical impulses to said surface of said body, via said electrodes,
   said series including a plurality of cycles, each of said cycles having a positive voltage pulse and a negative voltage pulse,
   wherein a frequency of said plurality of cycles is within a range of 60-150 cycles per second,
   wherein a time-averaged voltage amplitude ($Va_p$) of said positive voltage pulse, over an entire duration ($Tp_{positive}$) thereof, is 20-90 Volts,
   and wherein, in a ramp-up section of said positive voltage pulse,
   said positive voltage pulse attains at least 80% of said time-averaged voltage amplitude, within a time (T80) of 70-150 nanoseconds.

2. The device of claim 1, wherein T80 is at least 75 nanoseconds.

3. The device of claim 1, wherein T80 is at least 80 nanoseconds.

4. The device of claim 1, wherein T80 is at most 110 nanoseconds.

5. The device of claim 1, wherein said positive voltage pulse increases by at least 20 Volts, within 70 nanoseconds.

6. The device of claim 1, wherein said positive voltage pulse increases by at least 50 Volts, within 70 nanoseconds.

7. The device of claim 1, wherein an intermediate time (Ti) between said positive voltage pulse and said negative voltage pulse is at least 0.1 milliseconds.

8. The device of claim 7, wherein said intermediate time (Ti) is at most 1 millisecond.

9. The device of claim 1, wherein said positive pulse attains at least 80% of said time-averaged voltage amplitude for a pulse duration within a range of 80-120 microseconds.

10. The device of claim 1, wherein said positive pulse has a substantially constant voltage amplitude for a pulse duration within a range of 70-130 microseconds.

11. The device of claim 1, wherein said frequency of said plurality of cycles is within a range of 70-140 cycles per second.

12. The device of claim 1, wherein said negative voltage pulse is area-symmetric with respect to said positive voltage pulse, within 10 area %.

13. The device of claim 1, wherein said positive voltage pulse attains at least 90% of said time-averaged voltage amplitude, within 70-150 nanoseconds.

14. The device of claim 1, wherein said signal generator includes at least one of a voltage pre-amplifier and a voltage amplifier, adapted to amplify the voltage of a signal provided as input thereto.

15. The device of claim 1, wherein said signal generator includes an AC-to-DC converter adapted to produce a substantially DC signal.

16. The device of claim 1, wherein said signal generator includes a switching mechanism, responsive to said control unit, adapted to transform an input signal provided to said switching mechanism into said series of electrical impulses.

17. The device of claim 1, wherein said power supply comprises a low voltage power supply adapted to provide a nominal voltage of at most 10 volts.

18. The device of claim 1, wherein said device is portable while in said operative mode.

19. The device of claim 1, wherein said electrodes are adapted to contact said surface of the body of the user at a region of the body at which pain is experienced.

20. A non-invasive device for providing pain relief to a human user, the device comprising:
(a) at least two electrodes adapted to contact a surface of a body of the user;
(b) a control unit; and
(c) a signal generator, associated with said control unit and responsive thereto, said signal generator and said control unit adapted to operative connect to a power supply,
said signal generator adapted, in an operative mode, to provide a series of electrical impulses to said surface of said body, via said electrodes,
said series including a plurality of cycles, each of said cycles having a positive voltage pulse and a negative voltage pulse,
wherein a frequency of said plurality of cycles is within a range of 60-150 cycles per second,
wherein a time-averaged voltage amplitude ($Va_p$) of said positive voltage pulse, over an entire duration ($Tp_{positive}$) thereof, is 20-90 Volts,
wherein a ramp-up section of a said positive voltage pulse of cycles in a first subset of said plurality of cycles has a first ramp up time, a ramp-up section of a said positive voltage pulse of cycles in a second subset of said plurality of cycles, following said first subset, has a second ramp up time, shorter than said first ramp up time, and a ramp-up section of a said positive voltage pulse of cycles in a third subset of said plurality of cycles, following said second subset, has a third ramp up time, shorter than said second ramp up time,
and wherein, in said ramp-up section of said positive voltage pulse of said cycles in said third subset,
said positive voltage pulse attains at least 80% of said time-averaged voltage amplitude, within a time (T80) of 70-150 nanoseconds.

* * * * *